(12) United States Patent
Hoshino

(10) Patent No.: US 7,275,824 B2
(45) Date of Patent: Oct. 2, 2007

(54) FUNDUS CAMERA

(75) Inventor: Hidetaka Hoshino, Nukata-gun (JP)

(73) Assignee: Nidek Co. Ltd. (JP)

( * ) Notice: Subject to any disclaimer, the term of this patent is extended or adjusted under 35 U.S.C. 154(b) by 655 days.

(21) Appl. No.: 10/782,945

(22) Filed: Feb. 23, 2004

(65) Prior Publication Data

US 2004/0169818 A1 Sep. 2, 2004

(30) Foreign Application Priority Data

Feb. 28, 2003 (JP) ............... 2003-053293

(51) Int. Cl.
*A61B 3/14* (2006.01)
(52) U.S. Cl. ...................... 351/206; 351/208
(58) Field of Classification Search ........ 351/206–208, 351/214, 216, 217–218
See application file for complete search history.

(56) References Cited

U.S. PATENT DOCUMENTS

| | | | |
|---|---|---|---|
| 4,796,989 A | | 1/1989 | Fukuma et al. |
| 5,116,116 A | * | 5/1992 | Aizu et al. ............... 351/206 |
| 5,463,430 A | | 10/1995 | Isogai et al. |
| 6,056,404 A | | 5/2000 | Kawai et al. |
| 2001/0024263 A1 | | 9/2001 | Naniyo |

FOREIGN PATENT DOCUMENTS

| | | |
|---|---|---|
| EP | 1138256 A2 | 10/2001 |
| EP | 1183992 A2 | 3/2002 |
| JP | 2000-5131 | 11/2000 |

OTHER PUBLICATIONS

EPO Search Report Jun. 8, 2004.

* cited by examiner

*Primary Examiner*—Alicia M Harrington
(74) *Attorney, Agent, or Firm*—Rader Fishman & Grauer PLLC; Ronald P. Kananen

(57) ABSTRACT

A fundus camera for photographing a fundus of an eye to be examined has a system having an objective lens and a diaphragm arranged in a position approximately conjugate with a pupil with respect to the lens, for observing and photographing the fundus via the lens and the diaphragm, an optical path bifurcating member which is arranged on an optical path between the lens and the diaphragm, a system for observing an anterior segment of the eye via the lens and the optical path bifurcating member, and a correction member, which is arranged on an optical path of the fundus observation/photographing optical system, for correcting a deviation of an optical axis of the fundus observation/photographing optical system caused by arrangement of the optical path bifurcating member.

7 Claims, 5 Drawing Sheets ously arranged. Thereby, a possibility arises that a fundus image under an accurate alignment condition cannot be obtained.

FUNDUS CAMERA

BACKGROUND OF THE INVENTION

1. Field of the Invention

The present invention relates to a fundus camera for photographing a fundus of an eye to be examined.

2. Description of Related Art

For a fundus camera, accurate alignment with an eye to be examined (a patient's eye) and accurate focusing on a fundus are important to photograph the fundus favorably. As for the alignment, there is proposed a fundus camera, for example, in Japanese Patent Application Unexamined Publication No. 2000-5131, in which a movable optical path bifurcating (dividing) member is arranged on an optical path between an objective lens and an apertured mirror, and reflection light from an anterior segment of the eye is reflected by the optical path bifurcating member and is guided to image-pickup means for anterior-segment observation to perform alignment based on a picked up image of the anterior segment of the eye. In this apparatus, the optical path bifurcating member is flipped up (is removed from the optical path between the objective lens and the apertured mirror), so that the fundus is photographed by image-pickup means for photographing.

However, if the optical path bifurcating member is arranged on the optical path between the objective lens and the apertured mirror, an optical axis of an optical system for anterior-segment observation is deviated from that of an optical system for fundus observation and/or an optical system for photographing due to a thickness of the optical path bifurcating member. Thereby, a possibility arises that a fungus image under an accurate alignment condition cannot be obtained.

SUMMARY OF THE INVENTION

An object of the invention is to overcome the problems described above and to provide a fundus camera capable of obtaining a fundus image under an accurate alignment condition. Another object of the invention is to provide a fundus camera capable of obtaining a fundus image under an accurate focusing condition.

To achieve the objects and in accordance with the purpose of the present invention, a fundus camera has a fundus observation/photographing optical system, having an objective lens and a diaphragm arranged in a position approximately conjugate with a pupil of the eye with respect to the objective lens, for observing and photographing the fundus via the objective lens and the diaphragm, an optical path bifurcating member which is arranged on an optical path between the objective lens and the diaphragm, an anterior-segment observation optical system for observing an anterior segment of the eye via the objective lens and the optical path bifurcating member which is arranged on the optical path, and a correction member, which is arranged on an optical path of the fundus observation/photographing optical system, for correcting a deviation of an optical axis of the fundus observation/photographing optical system caused by arrangement of the optical path bifurcating member on the optical path.

Additional objects and advantages of the invention are set forth in the description which follows, are obvious from the description, or may be learned by practicing the invention. The objects and advantages of the invention may be realized and attained by the fundus camera in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
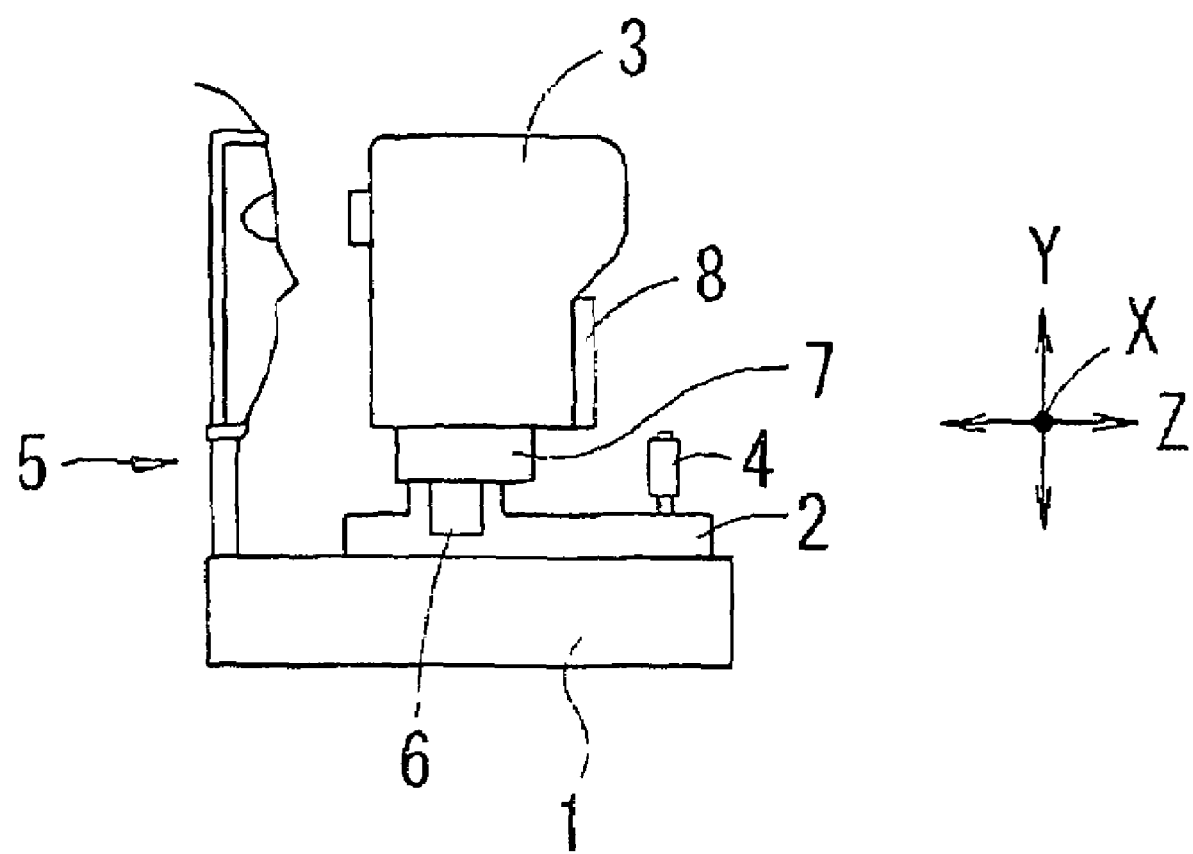
FIG. 1 is a view showing a schematic configuration of a fundus camera.

A detailed description of one preferred embodiment of a fundus camera embodied by the present invention is provided below with reference to the accompanying drawings. FIG. 1 is a view showing a schematic configuration of a fundus camera consistent with the preferred embodiment of the present invention.

The fundus camera is provided with a base 1, a moving base 2 being movable in, a right-and-left direction (hereinafter referred to as an "X direction") and a back-and-forth direction (hereinafter referred to as a "Z direction") with reference to the base 1 by operation of a joystick 4, a photographing unit 3 being movable in the right-and-left direction, an up-and-down direction (hereinafter referred to as a "Y direction"), and the back-and-forth direction With reference to the moving base 2 under control of a control unit 81, and a face supporting unit 5 fixedly arranged on the base 1 for supporting a face of an examinee. In an X-and Z-moving unit 7, a Z table movable in the Z direction is arranged on a Y table, an X table movable in the X direction is arranged on the Z table, and the photographing unit 3 is arranged on the X table. The X-and Z-moving unit 7 moves the X and Z tables by their respective moving mechanisms consisting of a motor and the like to move the photographing unit 3 in the X and Z directions. A Y moving unit 6 moves the Y table by its moving mechanism consisting of a motor and the like to move the photographing unit 3 in the Y direction. Besides, for this kind of three-dimensional moving mechanism, a known mechanism may be employed. Further, the photographing unit 3 is moved in the Y direction also by actuating the Y moving unit 6 through operation of a rotary knob of the joystick 4. A monitor 8 for displaying an observation image and a photographed image is provided on an examiner's side of the photographing unit 3.

Figure 2:
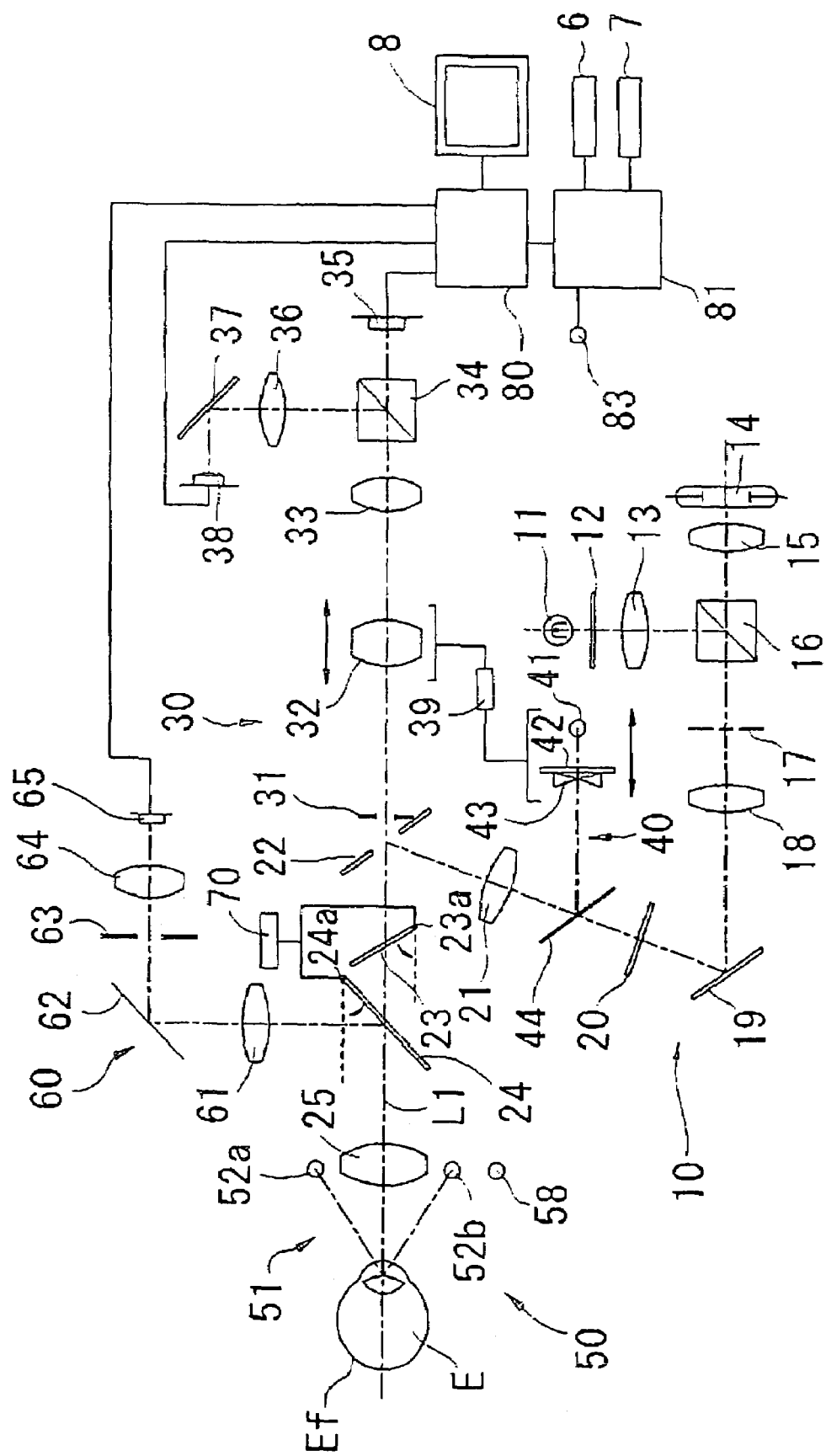
FIG. 2 is a view showing a schematic configuration of an optical system and a control system of the fundus camera.

FIG. 2 is a view showing a schematic configuration of an optical system and a control system housed in the photographing unit 3. The optical system roughly consists of an illumination optical system 10, a fundus observation/photographing optical system 30, a focus index (target) projection optical system 40, an alignment index (target) projection optical system 50, and an anterior-segment observation optical system 60.

<Illumination Optical System 10>

The illumination optical system 10 includes an illumination optical system for fundus observation and an illumination optical system for photographing. Illumination light emitted from an illumination light source 11 for fundus observation such as a halogen light is made infrared illumination light by an infrared transmission filter 12 which transmits light within an infrared range having a wavelength of approximately 750 nm to approximately 880 nm, and reflected by a dichroic mirror 16 via a condenser lens 13. The dichroic mirror 16 has a wavelength-selecting property of reflecting approximately all light within an infrared range and transmitting approximately all light within a visible range. The infrared illumination light reflected by the dichroic mirror 16 passes though a slit plate 17, a relay lens 18, a mirror 19, a black dot plate 20 having a black dot at its center, a half mirror 44 and a relay lens 21, and is reflected by an apertured mirror 22 to be projected onto an eye E of the examinee via an objective lens 25. The slit plate 17 has a pinhole aperture (opening) at a center part (on an optical axis) with a ring-slit aperture (opening) therearound. Besides, an infrared light source such as an infrared light-emitting diode may be used instead of the light source 11 such as a halogen light and the infrared transmission filter 12.

Visible illumination light emitted from a visible illumination light source 14 for photographing such as a flash light goes via a condenser lens 15 and is transmitted through the dichroic mirror 16 to be projected onto the eye E via the slit plate 17 to the objective lens 25.

<Fundus Observation/Photographing Optical System 30>

The fundus observation/photographing optical system 30 includes a fundus observation optical system and a photographing optical system. Infrared reflection light and visible reflection light from the eye E pass through the objective lens 25, an aperture (opening) of the apertured mirror 22, a photographing diaphragm 31 arranged in the vicinity of the aperture of the mirror 22, a focusing lens 32 and an image forming lens 33 to enter a dichroic mirror 34. The photographing diaphragm 31 is arranged in a position approximately conjugate with a pupil of the eye E with reference to the objective lens 25. The focusing lens 32 is arranged movable in an optical axis direction by a moving mechanism 39 consisting of a motor and the like. The dichroic mirror 34 has a wavelength-selecting property of reflecting approximately all light within the infrared range and transmits approximately all light within the visible range. The visible reflection light transmitted through the dichroic mirror 34 is photo-received on a CCD camera 35 for photographing having sensitivity to the visible range to form an image of the eye E. Also, the infrared reflection light reflected by the dichroic mirror 34 is photo-received on a CCD camera 38 for fundus observation having sensitivity to the infrared range via a relay lens 36 and a mirror 37 to form an image of the eye E. Incidentally, in a case where a fixation-index (target) projection (presenting) optical system is provided on the fundus observation optical system side, a dichroic mirror having a wavelength-selecting property of reflecting also a part of light within the visible range may be used instead of the dichroic mirror 34.

Figure 4:
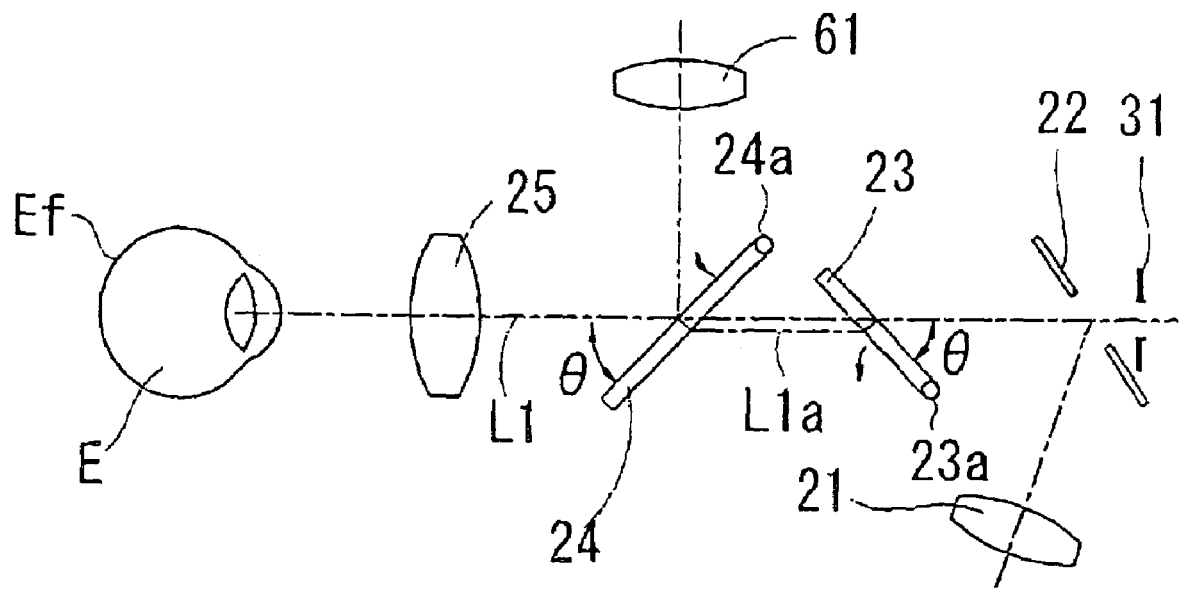
FIG. 4 is a view describing an occurrence of a deviation of an optical axis by insertion of a dichroic mirror, and correction thereof by insertion of a parallel glass plate.
Figure 7:
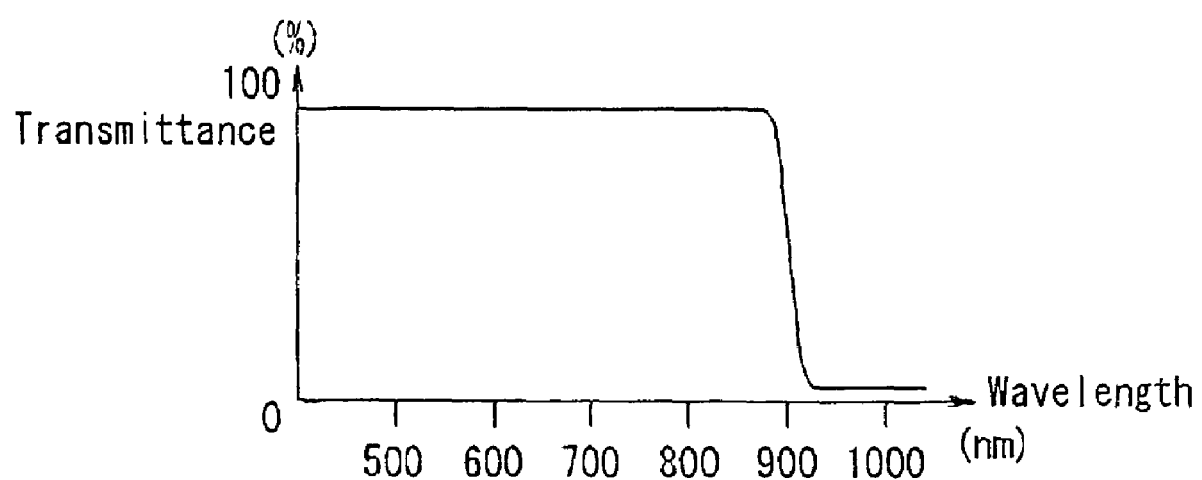
FIG. 7 is a view showing a wavelength-selecting property of the dichroic mirror.

On an optical path between the objective lens 25 and the apertured mirror 22 (the diaphragm 31), a movable dichroic mirror 24 is arranged as an optical path bifurcating (dividing) member. Further, on an optical path between the dichroic mirror 24 and the apertured mirror 22 (the diaphragm 31), a movable parallel glass plate 23 is arranged as a member for correcting a deviation of an optical axis caused by the dichroic mirror 24. The dichroic mirror 24 has a wavelength-selecting property (see FIG. 7) of reflecting approximately all light within an infrared range having a wavelength of approximately 900 nm or more including light from an illumination light source 58 for anterior-segment observation and that from the alignment index projection optical system 50 to be described later, and transmitting approximately all light within an infrared range having a wavelength of approximately 900 nm or less including light from the illumination optical system for fundus observation and that from the focus index projection optical system 40 to be described later. The glass plate 23 has approximately the same thickness and refractive index as the dichroic mirror 24. As shown in FIG. 4, the dichroic mirror 24 is arranged at an angle of inclination of θ with respect to an optical axis L1 of the fundus observation/photographing optical system 30 (the objective lens 25), and the glass plate 23 is arranged at an angle of inclination of 180° minus θ with respect to the optical axis L. Further, the center of an aperture (opening) of the photographing diaphragm 31 arranged approximately conjugate with the pupil of the eye E is placed on the optical axis L1, so that the infrared illumination light having a ring shape reflected from the anterior segment of the eye E does not enter the CCD camera 36. At the time of photographing, the dichroic mirror 24 and the glass plate 23 are flipped up synchronously having points 24a and 23a as supports respectively and removed from the optical path by an inserting and removing mechanism 70. Besides, a known mechanism such as a solenoid and cam (or motor and the like) may be used for the inserting and removing mechanism 70.

21 Focus Index Projection Optical System 40>

Infrared index light emitted from an infrared light source 41 for focus index projection such as an infrared light-emitting diode passes through a slit index (target) plate 42 and two deflection-angle prisms 43 attached to the index plate 42, and is reflected by the half mirror 44, and further passes through she relay lens 21 to the objective lens 25 to be projected onto the eye E. The light source 41 and the index plate 42 are moved in synchronization with the focusing lens 32 in the optical axis direction by the moving mechanism 39. Incidentally, the light source 41 emits infrared light having a center wavelength of approximately 880 nm.

<Alignment Index Projection optical System 50>

Figure 3:
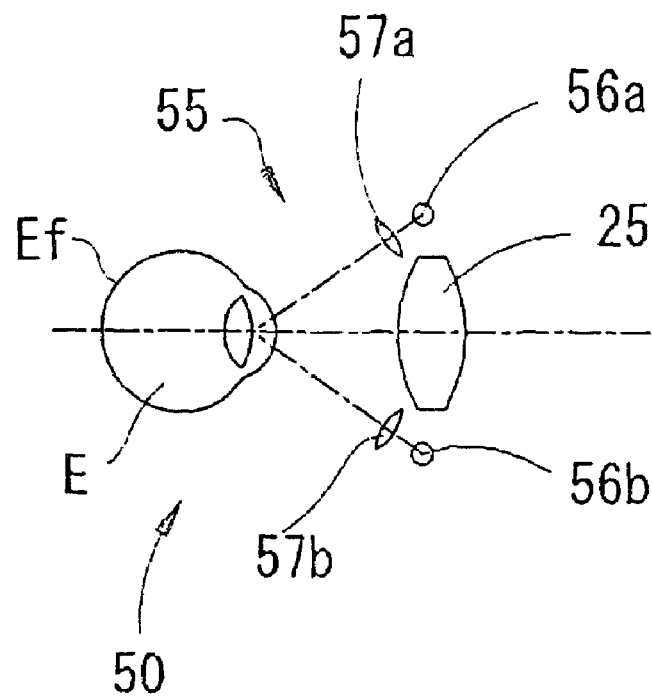
FIG. 3 is a view showing a schematic configuration of a second projection optical system in an alignment index (target) projection optical system.

The alignment index projection optical system 50 includes a first projection optical system 51 and a second projection optical system 55. The first projection optical system 51 includes infrared light sources 52a and 52b such as infrared light-emitting diodes arranged vertically symmetrical with respect to the optical axis L1 and projects infrared index light at a finite distance onto a cornea of the eye E. The second projection optical system 55 includes, as shown in FIG. 3 (a top view of an optical system portion of the objective lens 25), infrared light sources 56a and 56b such as infrared light-emitting diodes and collimating lenses 57a and 57b arranged laterally symmetrical with respect to the optical axis L1, and projects infrared index light at an infinite distance onto the cornea of the eye E. Incidentally, the light sources 52a, 52b, and 56a, 56b emit infrared light having a center wavelength of approximately 940 nm.

<Anterior-Segment Observation Optical System 60>

Infrared illumination light emitted from the illumination light source 58 for anterior-segment observation such as an infrared light-emitting diode is reflected by the dichroic mirror 24, arranged on the optical path, passes through a field lens 61, a mirror 62, a diaphragm 63 and a relay lens 64, and is photo-received on a COD camera 65 having sensitivity to the infrared range to form an image of the eye E. Besides, the light source 58 emits infrared light having a center wavelength of approximately 940 nm. Further, the CCD camera 65 doubles as image-pickup means for alignment index detection, which picks up an image of the anterior segment of the eye E formed by the light source 58 and an image of an alignment index formed by the alignment index projection optical system 50.

<Control System>

Image signals outputted from the CCD cameras 65, 38 and 35 are inputted to an image processing unit 80. The image processing unit 80 detects the image of the alignment index based on the image signal from the CCD camera 65 and the image of the focus index based on the image signal from the CCD camera 38. Further, the image processing unit 80 is connected to the monitor 8 to control an image to be displayed thereon. The control unit 81 is connected with the image processing unit 80, the Y moving unit 6, the X-and Z-moving unit 7, the joystick 4, the moving mechanism 39, the inserting and removing mechanism 70, a photographing switch 83, the respective light sources, and the like. (In FIG. 2, connection lines are partly not illustrated.)

Figure 5:
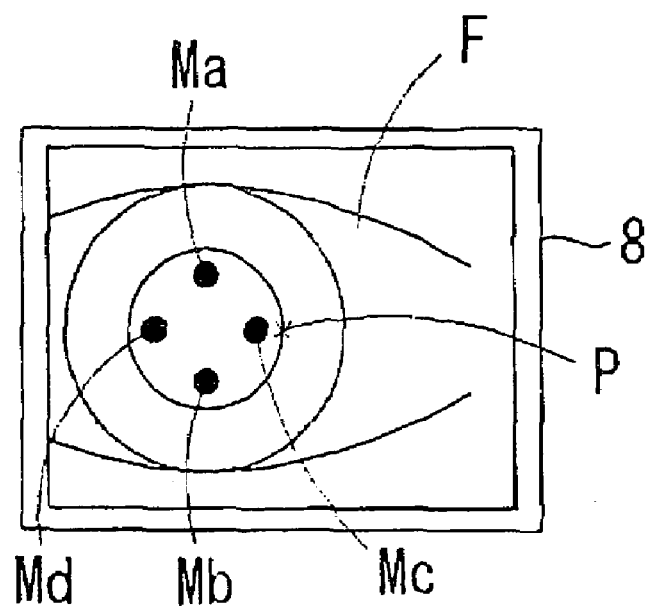
FIG. 5 is a view showing an example of an image of an anterior segment of an eye picked up by a CCD camera for anterior-segment observation.

In the apparatus having a constitution as above, the operation thereof will be described hereinafter. At the time of photographing a fundus Ef of the eye E, initially, the eye E is aligned with the photographing unit 3 while observing the anterior segment of the eye E. Here, a case will be described where automatic alignment is selected using a switch unillustrated. At the time of the observation of the anterior segment of the eye E, the dichroic mirror 24 and the glass plate 23 are inserted into the optical path of the fundus observation/photographing optical system 30 (the optical path between the objective lens 25 and the apertured mirror 22). The image of the anterior segment of the eye E formed by the light source 58 is reflected by the dichroic mirror 24 and picked up by the CCD camera 65. In addition, the image of the alignment index formed by the alignment index projection optical system 50 is also reflected by the dichroic mirror 24 and picked up by the CCD camera 65. The image signal outputted from the CCD camera 65 is inputted into the image processing unit 80, and an image F of the anterior segment of the eye E and the image of the alignment index are displayed on the monitor 9 (see FIG. 5). In FIG. 5, the index images Ma and Mb vertically positioned are the alignment index images at a finite distance formed by the first projection optical system 51, and the index images Mc and Md horizontally positioned are the alignment index images at an infinite distance formed by the second projection optical system 55. P is a reticle for alignment.

The examiner operates the joystick 4 to move the moving base 2 in the X and Z directions and the photographing unit 3 in the Y direction so that the image F of the anterior segment of the eye E is placed in the center of the monitor 8. Then, when the four index images Ma to Md picked up by the CCD camera 65 are detectable to the image processing unit 80, the automatic alignment through driving and control of the X-and Z-moving unit 7 and the Y moving unit 6 is actuated. The image processing unit 80 detects a corneal center based on an intersection point of a segment between the index images Ma and Mb and a segment between the index images Mc and Md to obtain a deviation (i.e., direction and amount of deviation) from an alignment reference in the X and Y directions. Upon receiving an output signal from the image processing unit 80, the control unit 81 drives and controls the X-and Z-moving unit 7 and the Y moving unit 6 to move the photographing unit 3 in the X and Y directions so that the deviation in the X and Y directions falls within a predetermined allowable range. Further, the image processing unit 80 compares a distance, between the index images Ma and Mb with that between the index images Mc and Md to detect an alignment condition in the Z direction. It utilizes a characteristic that in the case of forming corneal reflection images using a light source at an infinite distance and a light source at a finite distance, if a working distance is changed, a height of the image formed with the light source at a finite distance changes while that formed with the light source at an infinite distance does not change. (For the details, see U.S. Pat. No. 5,463,430 corresponding to Japanese Patent Application Unexamined Publication No. Hei6-46999.) Upon receiving the output signal from the image processing unit 80, the control unit 81 drives and controls the X-and Z-moving unit 7 to move the photographing unit 3 in the Z direction so that the alignment condition in the Z direction falls within a predetermined allowable range.

Incidentally, in the case of manual alignment, the examiner may perform the alignment in the X and Y directions by operating the joystick 4 while observing a positional relationship between the index images Ma to Md and the reticle P. Also, the examiner may perform the alignment in the Z direction by operating the joystick 4 while observing a mark for guidance displayed on the monitor 8, based on a detection result on the working distance obtained with the index images Ma to Md.

The infrared illumination light from the illumination optical system for fundus observation is reflected by the apertured mirror 22, is transmitted through the glass plate 23 and the dichroic mirror 24, converges once in the vicinity of the pupil of the eye E by the objective lens 25, and is diffused to be projected onto the fundus Ef. Also, the infrared index light from the focus index projection optical system 40 is reflected by the apertured mirror 22, is transmitted through the glass plate 23 and the dichroic mirror 24 to be projected onto the fundus Ef via the objective lens 25.

An image of the fundus Ef and an image of a focus index pass through the dichroic mirror 24 and the glass plate 23 to be picked up by the CCD camera 38. The image signal outputted from the COD camera 38 is inputted to the image processing unit 80, and the images of the fundus Ef and the focus index are displayed on the monitor 8. At this time, as shown in FIG. 4, the insertion of the dichroic mirror 24 causes the optical axis L1 of the fundus observation/photographing optical system 30 to be a deviated optical axis L1a; however, the deviation is corrected by inserting the glass plate 23. Therefore, a position of the observation image of the anterior segment of the eye E through the CCD camera 65 and a position of the observation image of the fundus Ef through the CCD camera 38 correspond to each other.

If the glass plate 23 is not inserted, the deviated optical axis L1a does not pass through the center of the aperture of the photographing diaphragm 31. In such an event, a center of the infrared illumination light having a ring shape reflected form the anterior segment of the eye E is deviated from the center of the aperture of the photographing diaphragm 31, and the infrared reflection light from the anterior segment of the eye E enters the CCD camera 38 even in a state where the alignment is completed. As a result, flare light tends to appear in the observation image of the fungus Ef, the fundus Ef cannot be observed favorably, and the image of the focus index becomes difficult to detect.

Figure 6:
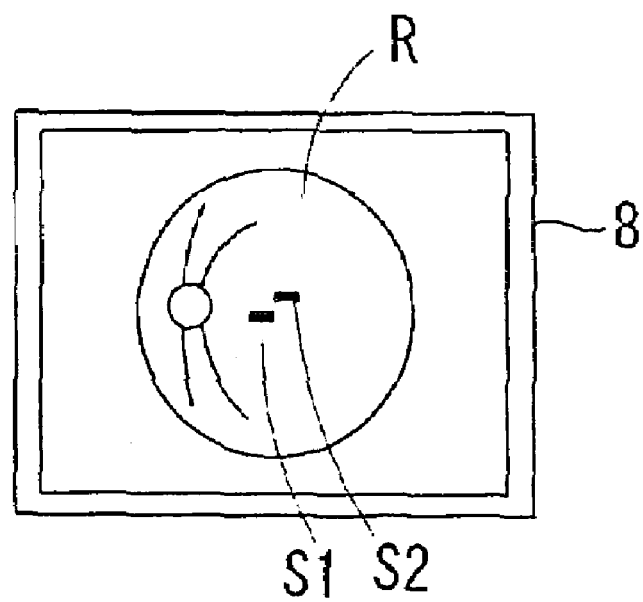
FIG. 6 is a view showing an example of a fundus image picked up by a CCD camera for fundus observation.

FIG. 6 is a view showing an example of the image of the fundus Ef picked up by the CCD camera 38, in which index images S1 and S2 are formed at the center of an image R by the focus index projection optical system 40. When the fundus Ef is out of focus, the index images S1 and S2 are separated, and when the fundus Ef is brought into focus, the index images S1 and S2 coincide with each other. The image processing unit 80 detects the index images S1 and S2 and sends their separation information to the control unit 81. Then, the control unit 81 drives and controls the moving mechanism 39 based on the separation information of the index images S1 and S2 to move the focusing lens 32, the light source and the index plate 42 in the optical axis direction for bringing focus on the fundus Ef.

When the fundus Ef is brought into focus, the image to be displayed on the monitor 8 is switched to the fundus image picked up by the CCD camera 38. Alternatively, the image of the anterior segment of the eye E picked up by the CCD camera 65 may be switched to the fundus image upon completion of the alignment. Further, a constitution may be employed where the images of both the anterior segment of the eye E and the fundus Ef are displayed on the monitor 8 and the examiner selectively displays either of them under magnification. Incidentally, the detection of the alignment index images by the CCD camera 65 is sequentially performed and tracking movement of the photographing unit 3 for the eye E is also performed. The examiner guides the fundus Ef by moving a fixation lamp not illustrated while identifying the fundus image displayed on the monitor 8. At this time, since the optical axis L1a deviated due to the dichroic mirror 24 is corrected by the glass plate 23 to be the optical axis L1 passing through the center of the aperture of the photographing diaphragm 31 as described above, a favorable fundus image without flare may be observed.

When a desired portion of the fundus Ef becomes observable, the photographing switch 83 is pressed to perform photographing. The control unit 81 drives and controls the inserting and removing mechanism 70 to remove the dichroic mirror 24 and the glass plate 23 from the optical path and make the light source 14 emit light. Thereby, the Fundus Ef is illuminated with the visible illumination light, and the visible reflection light from the fundus Ef is photo-received on the CCD camera 35 via the objective lens 25 to the dichroic mirror 34 to form the image of the fundus Ef. The image processing unit 80 switches the monitor 8 to display the fundus image picked up by the COD camera 35.

Incidentally, the glass plate 23 is not limited to the one in the present embodiment, and it is sufficient to correct the deviation of the optical axis caused by the optical path bifurcating member (dichroic mirror 24). In other words, material (the refractive index) and form (the thickness) of the glass plate 23 are not limited to those in the present embodiment.

As described above, according to the present invention, the fundus image under the accurate alignment condition may be obtained. In addition, the fundus image under the accurate focusing condition may be obtained.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed:

1. A fundus camera for photographing a fundus of an eye to be examined, the camera comprising:
   a fundus observation/photographing optical system, having an objective lens and a diaphragm arranged in a position approximately conjugate with a pupil of the eye with respect to the objective lens, for observing and photographing the fundus via the objective lens and the diaphragm;
   an optical path bifurcating member which is arranged on an optical path between the objective lens and the diaphragm;
   an anterior-segment observation optical system for observing an anterior segment of the eye via the objective lens and the optical path bifurcating member which is arranged on the optical path; and
   a correction member, which is arranged on an optical path of the fundus observation/photographing optical system, for correcting a deviation of an optical axis of the fundus observation/photographing optical system caused by arrangement of the optical path bifurcating member on the optical path, and further comprising
   an inserting and removing unit which performs insertion and removal of the optical path bifurcating member and the correction member with respect to the optical path.

2. The fundus camera according to claim 1, wherein the correction member has approximately same thickness and refractive index as the optical path bifurcating member, and is arranged, assuming that an arrangement angle of the optical path bifurcating member with respect to the optical axis of the fundus observation/photographing optical system is .theta., at an arrangement angle of 180.degree. minus .theta. with respect to said optical axis.

3. A fundus camera for photographing a fundus of an eye to be examined, the camera comprising:
   a fundus observation/photographing optical system, having an objective lens and a diaphragm arranged in a position approximately conjugate with a pupil of the eye with respect to the objective lens, for observing and photographing the fundus via the objective lens and the diaphragm;
   an optical path bifurcating member which is arranged on an optical path between the objective lens and the diaphragm;
   an anterior-segment observation optical system for observing an anterior segment of the eye via the objective lens and the optical path bifurcating member which is arranged on the optical path; and
   a correction member, which is arranged on an optical path of the fundus observation/photographing optical system, for correcting a deviation of an optical axis of the fundus observation/photographing optical system caused by arrangement of the optical path bifurcating member on the optical path, and further comprising:
   an illumination optical system for fundus observation, for projecting illumination light for fundus observation;
   an alignment index projection optical system for projecting alignment index light onto the anterior segment of the eye; and
   a focus index projection optical system for projecting focus index light onto the fundus, wherein the optical path bifurcating member is a wavelength-selecting mirror having a wavelength-selecting property of reflecting a wavelength of the alignment index light and transmitting a wavelength of the illumination light for fundus observation and a wavelength of the focus index light.

4. The fundus camera according to claim 3, further comprising an illumination optical system for anterior-segment observation, for projecting illumination light for anterior-segment observation, wherein the wavelength-selecting mirror has a wavelength-selecting property of reflecting a wavelength of the illumination light for anterior-segment observation.

5. The fundus camera according to claim 4, wherein
the fundus observation/photographing optical system has a first image-pickup element which picks up a fundus observation image and a focus index image, and
the anterior-segment observation optical system has a second image-pickup element which picks up an anterior-segment observation image and an alignment index image.

6. The fundus camera according to claim 5, further comprising:
an alignment unit which performs alignment of the fundus observation/photographing optical system with the eye based on the alignment index image picked up; and
a focusing unit which performs focusing of the fundus observation/photographing optical system based on the focus index image picked up.

7. A fundus camera for photographing a fundus of an eye to be examined, the camera comprising:
a fundus observation/photographing optical system, having an objective lens and a diaphragm arranged in a position approximately conjugate with a pupil of the eye with respect to the objective lens, for observing and photographing the fundus via the objective lens and the diaphragm;
an optical path bifurcating member which is arranged on an optical path between the objective lens and the diaphragm;
an anterior-segment observation optical system for observing an anterior segment of the eye via the objective lens and the optical path bifurcating member which is arranged on the optical path; and
a correction member, which is arranged on an optical path of the fundus observation/photographing optical system, for correcting a deviation of an optical axis of the fundus observation/photographing optical system caused by arrangement of the optical path bifurcating member on the optical path, and further comprising:
an alignment index projection optical system for projecting alignment index light onto the anterior segment of the eye;
a focus index projection optical system for projecting focus index light onto the fundus;
an alignment unit which performs alignment of the fundus observation/photographing optical system with the eye based on a detection result on an alignment index image formed on the anterior segment of the eye; and
a focusing unit which performs focusing of the fundus observation/photographing optical system based on a detection result on a focus index image formed on the fundus.

* * * * *